United States Patent [19]

Asmussen et al.

[11] Patent Number: 5,869,652

[45] Date of Patent: Feb. 9, 1999

[54] PROCESS FOR PRODUCING ACTIVE SUBSTANCES FROM UNUSED OR DISCARDED DEVICES FOR THE TRANSDERMAL ADMINISTRATION

[75] Inventors: Bodo Asmussen, Bendorf; Hans-Rainer Hoffmann; Walter Müller, both of Neuwied, all of Germany

[73] Assignee: LTS Lohmann Therapie-Systeme GmbH, Germany

[21] Appl. No.: 983,029

[22] PCT Filed: Jun. 24, 1996

[86] PCT No.: PCT/EP96/02734

§ 371 Date: Jan. 2, 1998

§ 102(e) Date: Jan. 2, 1998

[87] PCT Pub. No.: WO97/02100

PCT Pub. Date: Jan. 23, 1997

[30] Foreign Application Priority Data

Jul. 1, 1995 [DE] Germany ......................... 195 24 083.9

[51] Int. Cl.$^6$ ............................ C07D 223/14; B09B 3/00; C07C 217/70

[52] U.S. Cl. ............................. 540/484; 540/2; 540/576; 540/581; 540/612

[58] Field of Search ..................................... 540/484, 576, 540/581, 612

[56] References Cited

U.S. PATENT DOCUMENTS

| | | | |
|---|---|---|---|
| 4,543,364 | 9/1985 | Nankee et al. | 521/40 |
| 5,288,408 | 2/1994 | Schmidt et al. | 210/634 |
| 5,461,147 | 10/1995 | Hou et al. | 540/576 |

*Primary Examiner*—Mukund J. Shah
*Assistant Examiner*—Pavanaram K. Sripada
*Attorney, Agent, or Firm*—Wenderoth, Lind & Ponack, L.L.P.

[57] ABSTRACT

In a process for reprocessing devices for the transdermal application of active substances or their process waste, active substance-containing components are brought into solution and the active substances are recovered therefrom.

14 Claims, No Drawings

PROCESS FOR PRODUCING ACTIVE SUBSTANCES FROM UNUSED OR DISCARDED DEVICES FOR THE TRANSDERMAL ADMINISTRATION

This application is a 371 of PCT/EP 96/02734.

The present invention relates to a process for recovering active substances from unused or discarded devices for the transdermal application of active substances and/or their process waste, wherein the active substances contained in said devices are usually present in combination with polymeric films and polymeric sheets.

Devices for the transdermal application may be subdivided into two types:
a. systems releasing the active substance to the skin or organism by passive diffusion, and
b. systems releasing the active substances to the skin or organism under the action or by the aid of electric currents.

Systems based on passive diffusion are the so-called Transdermal Therapeutic Systems (TTS). They may be classified into the so-called matrix systems and the reservoir systems. In matrix systems, the active substance is dissolved in polymer films, or a certain portion is additionally suspended in crystalline-form or in the form of microcapsules. In the simplest case these systems therefore consist of a backing layer which is substantially impermeable to the active substance, the active substance-containing and preferably self-adhesive matrix, and a protective sheet to be removed prior to use.

Reservoir systems comprise the active substance in a fluid reservoir. The active substance may be present in a completely or only partially dissolved form. In the simplest case these systems consist of a backing layer which is impermeable to the substances contained in the reservoir, and a membrane at least permeable to the active substance and preferably provided with an adhesive film for skin application of the system.

Systems releasing the active substance to the skin or the organism under application of electric current may have various structures. They are particularly used for active substances which—owing to their chemico-physical properties—cannot penetrate the skin in a sufficient amount by means of passive diffusion. For known reasons an unspent active substance portion remains in each worn TTS. Such active substance-containing waste products represent a toxicological or ecological risk and must therefore be disposed of as hazardous waste at considerable expense. On the other hand, these waste products still contain very expensive and valuable ingredients or active substances originating from medicinal preparations, and in some cases it appears economically appropriate to recover these ingredients. One reason why the economic considerations to be taken into account in this connection are in favor of recovering active substances is that the support which is then substantially free of active substance is no longer regarded as hazardous waste and can therefore be disposed of at minimum cost.

The same applies to unused TTSs and their process waste, which inevitably results in some production methods, or to imperfect batches, which cannot always be avoided.

A number of recycling methods is known in the art, in particular recycling of waste products comprising adhesive-coated sheet material. DE 42 09 676, for example, describes a method of recycling pressure-sensitive self-adhesive material having an embossed stripfilm, in particular of PET-sheet material, laminated with ethylene-terephthalate-isophthalate copolyester. DE 42 21 681 describes a method of recycling polyethylene, polypropylene, or polystyrene adhesives on label waste products. DE 40 37 562 describes a recycling of adhesive-coated plastic films by repeated kneading in a solvent, drainage in a screw conveyor, and repeated passage of the remaining material in the same procedure.

DE 40 37 562 describes a process for recycling plastic sheets which are coated with adhesive and present in chip form by separating the plastic material and the adhesive. In a first stage, the sheet chips, placed in a solvent for the adhesive to disperse the adhesive adhering to the sheet chips, are agitated with the solvent for a predetermined period under mechanical action. Subsequently, the adhesive dispersed in the solvent is separated from the sheet shreds under mechanical action. In a second, similar stage fresh solvent is supplied to the sheet chips of the first stage, and the solvent-adhesive-dispersion of the second stage is fed to the first stage.

It is the object of the present invention to provide a process with which it is possible in a cost-efficient manner to reprocess waste products of medical formulations, and in particular unused devices for the transdermal application of active substances or those devices discarded after wearing, so-called TTSs, for recovery of active substances contained therein, and at the same time to make the disposal of the supporting material, after withdrawal of its active substance content, economically efficient.

The solution of the object is achieved in a process of the above-mentioned kind by means of the present invention by the fact that the active substance-containing material is brought into solution in a solvent, and that the active substance is recovered therefrom.

The proposed method is ecologically safe, feasible with economical means, and provides recovery of a valuable raw active substance, on the one hand; on the other hand, a fraction of solids or supporting materials which is substantially free of ingredients, environmentally neutral, and therefore easy to dispose of is obtained. The supports or the other residues of the process can be recycled further according to methods known in the art.

According to an embodiment of the process the materials to be reprocessed are subjected to a pretreatment wherein they are sorted into preferably pure-grade fractions, relative to the active substance, which have been separated from foreign matter, such as supporting and/or protective films, packaging material, etc., and the active substance-containing material is concentrated. According to another embodiment of the present invention the materials to be subjected to reprocessing (also referred to as "waste products") are delivered to the recycling station in packages or packaging aids, and the packages or packaging aids have a distinct identification relating to the contents, for example, in the form of a color pattern or coded field suitable for automatic sorting. Such a coded field permits fully-automatic sorting of the coded package into pure-grade ingredients, for example, like the sorting of mail. This avoids expensive manual operation, and sorting can be carried out perfectly. This is of vital importance for a process for recovering active substances, for example, from TTS-scrap. To support dissolution of the active substance-containing material in a solvent, it may be advantageous to reduce the waste products in size, if necessary under low-temperature embrittlement. Among other things, deep-freezing with liquid nitrogen has the additional advantage that waste materials thus cooled do not release noxious substances to the environment when comminuted. A size reduction which can thus be achieved, for example, to particle sizes of below 2 mm, results—because of the enlarged active surface—in an easier and even more complete dissolution of the comminuted material in the solvent bath; or the active substance can thus be recovered by maceration, percolation, or fluidized-bed extraction. To dissolve the active substance-containing material, a measure which is essential for the present invention provides that a solvent or solvent mixture is used that has a comparatively low dissolving capacity for adhesives and a preferred solubilizing power for the active substance. Further isolation of the active substance from the solution is then possible, for example, by liquid-liquid extraction, countercurrent extraction, or other suitable methods. To recover the active substance from the solution it may furthermore be provided that the recovery is carried out by precipitation or chemical intermediary bonding, or by deposition of foreign compounds, evaporation, distillation, or other suitable separation methods.

When the active substances are extracted with solvents or solvent mixtures, it is advisable for basic active substances to use water having an acidic pH or an acidified water/alcohol mixture, and for acid active substances to set a basic pH-value. For active substances without acid or basic functional groups it is quite obvious to use neutral water/alcohol mixtures. The active substances can then be removed from these mixtures by changing the pH-value or by adding water, or by means of liquid-liquid extraction. The use of substantially aqueous solvents has the additional advantage that substantially lipophilic auxiliary agents are coextracted to an only small extent. Supercritical gases may also be used as solvent to extract the active substance. Their particular advantage lies in the fact that their solubilizing power, temperature, and pressure, as well as the admixture of additional solvents can be influenced within certain limits, and that it is very easy to separate the extracted components from the solvent. Since supercritical gases have a very low viscosity and can therefore diffuse into the product to be extracted very rapidly, they are particularly suitable to extract active substances from polymeric materials. Because of the good environmental compatibility, low price, and ease of handling supercritical carbon dioxide is particularly suitable for this purpose. Since the solids are substantially free of toxicologically or ecologically risky materials after withdrawal of active substances, the solids thus separated can easily be disposed of as environmentally neutral waste products, for example, by incineration or dumping. In comparison with the dumping costs for hazardous waste, the costs saved exceed the expenses for the recovery process according to the present invention. There is the chance for a cost-effective active substance recovery process. The active and ingredient substances dissolved in the solvent can be recovered from the solution or the solvent mixtures by means of known thermal purification methods, such as distillation or rectification, in a manner known and proven per se with comparatively low capital and power expenditure.

Moreover, it is provided that the raw active substance recovered from the solution is reprocessed into a pharmaceutically pure active substance in a final operation.

The methods suitable for this purpose are known to the skilled artisan, examples thereof include recrystallization, or preparative high- or medium-pressure chromatography.

The process is appropriate and economically advantageous, and it achieves the object stated at the beginning in an optimum manner.

Active substances having a hormonal action, estradiol, estradiol derivatives, gestagens, gestagen derivatives or their mixtures, morphine or morphine derivatives, buprenorphine, physostigmine, scopolamine, galanthamine, may in particular be recovered by selection of the processing parameters. The recovered substances may then be used again according to their pharmaceutical action as analgesics, as well as for the treatment of senile dementia, high blood pressure, arrhythmia, vascular diseases, addictions, hyperlipidaemias, psychological disturbances, to influence blood coagulation, disorders in dietary habit, or dysglycemia.

We claim:

1. A process for the recovery of active substances from unused or discarded devices for the transdermal application of active substances (TTS) and/or their process waste, the unused devices or waste products having as active substance-containing material either a matrix, which optionally may be pressure-sensitive adhesive, or a reservoir, wherein the active substance is comprised as a homogeneous mixture, in the form of microcapsules or crystals, or as a liquid solution, or being present in combination with polymeric films and polymeric sheets, characterized in that the active substance(s) and optionally further components is/are brought into solution in a solvent, and that the active substance is recovered therefrom.

2. The process according to claim 1 characterized in that the unused or discarded TTSs or the waste products are subjected to a pretreatment sorting them into pure-grade fractions which have been separated from foreign matter, such as supporting and/or protective sheets, packaging material, and that the active substance-containing material is concentrated.

3. The process according to claim 1 or 2 characterized in that the unused or discarded TTSs or the waste products, packed in packages or packaging aids, are delivered to a recycling station, and that the package or packaging aids have a distinct, content-indicating identification, for example, in the form of a color pattern or coded field suitable for automatic sorting.

4. The process according to claim 1 or 2 characterized in that the unused or discarded TTSs or the waste products are subjected to a size reduction, optionally under low-temperature embrittlement.

5. The process according to claim 1 or 2 characterized in that a solvent or solvent mixture is used to dissolve the active substance or active substances, which has a comparatively low dissolving capacity for adhesives and other components of the TTS and a preferred solubilizing power for the active substance/s.

6. The process according to claim 5 characterized in that the dissolution of the substance is carried out under intensive stirring and optionally at an elevated temperature.

7. The process according to claim 1 characterized in that the extraction of the active substance from the solution is carried out by means of
    liquid-liquid extraction
    maceration or percolation
    countercurrent extraction
    fluidized-bed extraction
or other suitable methods.

8. The process according to claim 1 characterized in that the recovery of the active substance from the solution is carried out by means of precipitation, chemical intermediary bonding, deposition of foreign compounds, evaporation, distillation, or other suitable separation methods.

9. The process according to claim 5 characterized in that water with an acidic pH or an acidified water/alcohol mixture is used to dissolve basic active substances.

10. The process according to claim 5 characterized in that neutral or basified water/alcohol mixtures are used to dissolve the active substances.

11. The process according to claim 1 characterized in that supercritical gases, preferably carbon dioxide, are used to dissolve the active substance or active substances.

12. The process according to claim 1 characterized in that the active substance/s recovered from the solution is/are reprocessed to pharmaceutically pure active substance in a final operation.

13. The process according to claim 1 to characterized in that the rectification of the raw active substances is effected by separation methods by distillation, or by high-pressure extraction with supercritical gases, preferably $CO_2$.

14. The process according to claim 9 characterized in that the active substances are removed from the water/alcohol/active substance mixtures by changing the pH-value or by adding water, or by means of liquid-liquid extraction.

* * * * *